United States Patent [19]

Chase et al.

[11] Patent Number: 4,490,553
[45] Date of Patent: Dec. 25, 1984

[54] PROCESS FOR PRODUCTION OF ETHYL ACRYLATE

[75] Inventors: Joseph D. Chase, Robstown; William W. Wilkison, Richardson, both of Tex.

[73] Assignee: Celanese Corporation, New York, N.Y.

[21] Appl. No.: 182,553

[22] Filed: Aug. 29, 1980

[51] Int. Cl.³ .................... C07C 67/04; C07C 67/54
[52] U.S. Cl. .................................. 560/205; 560/218; 203/89
[58] Field of Search .................. 560/205, 218. 248; 203/89; 159/49

[56] References Cited

U.S. PATENT DOCUMENTS

| | | | |
|---|---|---|---|
| 3,292,683 | 12/1966 | Buchi et al. | 159/6 |
| 3,464,478 | 9/1969 | Ueda et al. | 159/6 |
| 3,539,621 | 11/1970 | Cipollone et al. | 560/205 |
| 3,695,327 | 10/1972 | Widmer | 203/89 |
| 3,703,539 | 11/1972 | Di Liddo | 560/217 |
| 3,895,076 | 7/1975 | Van Duyne et al. | 560/205 |

OTHER PUBLICATIONS

*Chemical Engineering,* Sep. 13, 1965, pp. 175–190.

*Primary Examiner*—Natalie Trousof
*Assistant Examiner*—L. Hendriksen
*Attorney, Agent, or Firm*—L. I. Grim

[57] ABSTRACT

A process is provided for the continuous production of ethyl acrylate from ethylene and acrylic acid in the presence of sulfuric acid. The process includes the removal of impurities from the reaction system by passing minor portions of sulfuric acid residue from the process through a wiped-film evaporator whose initial sections are heated to a specific temperature range and whose last or withdrawal sections are cooled to a specific temperature range. The treated sulfuric acid residue is withdrawn from the reaction system. This treatment prevents foaming of the sulfuric acid residue. If foaming of the sulfuric acid residue occurs, the foamed residue can back up into the reaction system requiring a shutdown of the entire process. The improvement of this process is the passing of the ethyl acrylate product residue from the finishing distillation tower into the wiped-film evaporator at the same time that the sulfuric acid residue is being treated. The treatment of the ethyl acrylate product residue recovers additional ethyl acrylate product and acrylic acid starting material from the wiped-film evaporator while the remainder of the ethyl acrylate product residue containing polymerization initiators which in turn can cause undesirable polymerized product is removed from the reaction system.

3 Claims, 2 Drawing Figures

4,490,553

PROCESS FOR PRODUCTION OF ETHYL ACRYLATE

BACKGROUND OF THE INVENTION

Processes for the production of ethyl acrylate by interacting acrylic acid with ethylene in the presence of sulfuric acid are well known; see for example, U.S. Pat. No. 3,703,539, issued Nov. 21, 1972 to DiLiddo; U.S. Pat. No. 3,539,621, issued Nov. 10, 1970 to Cipollone et al; and U.S. Pat. No. 3,894,076, issued July 8, 1975 to Van Duyne et al. As described in these and other references, the reaction is believed to involve the formation of intermediate sulfates from the reaction of ethylene with sulfuric acid. These sulfates further react with acrylic acid to form ethyl acrylate. To provide a product in good overall yields with high carbon efficiencies, unreacted ethylene, acrylic acid and the sulfuric acid residue must be recycled to the reactor. The residence times of some of these reactants can be long enough to result in the formation of partially polymerized products which can plug the process equipment. Additionally, these processes operating on a continuous basis for extended periods of time produce impurities in the reaction system which must be efficiently removed.

A method which has been used to remove impurities formed in the ethylene-acrylic acid reaction to ethyl acrylate is to pass a minor portion of the sulfuric acid residue recycled to the ethylene-acrylic acid reactor to a wiped-film evaporator whose initial stages are heated to enable the sulfuric acid residue to reach a temperature in the range from about 300° F. to about 360° F. and whose last or withdrawal section(s) are cooled to enable the sulfuric acid residue to reach a temperature in the range from about 230° F. to about 280° F. The spent sulfuric acid residue is thereby removed from the reaction system.

In the chemical industry, it is common to use a wiped-film evaporator for processing highly viscous solutions and for vacuum evaporation. Typical of the units that can be used and are known are the types described in a three part report in *Chemical Engineering*, Sept. 13, 1965, pages 175-190, entitled "Agitated Thin-Film Evaporators". Modifications of these types of evaporators are described in the art, for example, in U.S. Pat. No. 3,292,683 entitled "Wiped Falling Film Evaporator" issued Dec. 20, 1966 to Buchi et al; U.S. Pat. No. 3,464,478 entitled "Horizontal-Type High Vacuum Film Evaporator For Highly Viscous Solutions" issued Sept. 2, 1969 to Tomoharu Ueda et al; U.S. Pat. No. 3,695,327 entitled "Wiped Thin Film Evaporation and Treatment Process" issued Oct. 3, 1972 to Widmer; among others. This equipment is normally used to separate highly viscous materials from volatile materials with the objective to separate the materials at the highest efficiencies in the least amount of time. Under these conditions, these evaporators are maintained at the highest possible temperatures for the most efficient periods of time. None of the processes and equipment known in the use of wiped-film evaporators area are known to evaporate and cool within the same unit. In the process of producing ethyl acrylate by the reaction of ethylene and acrylic acid in the presence of sulfuric acid, it is the technique of heating the initial stages of the evaporator and cooling the last or withdrawal section(s) which provides the highly efficient and desirable process of separating the highly viscous sulfuric acid residue from the volatile products such as ethyl acrylate and acrylic acid while maintaining foaming of the evaporating material at a workable and controllable minimum.

Cooling the last or withdrawal section(s) of the wiped-film evaporator substantially eliminates foaming of the spent sulfuric acid residue. If the sulfuric acid residue is not cooled, foaming of the residue in the wiped-film evaporator can be sufficiently severe that the foam can back through the lines leading to the wiped-film evaporator leading to a shut down of the wiped-film evaporator. This results in significant acrylic acid and ethylene efficiency losses and can lead to total process shut down if adequate sulfuric acid purge is not withdrawn from the system. Furthermore, if various impurities are not removed from the system, increased polymer formation can occur in the ethylene-acrylic acid reactor which can lead to plugging of the process equipment. It has been discovered that significant amounts of polymerization initiators produced in the ethyl acrylate production can be removed from the reaction process by passing at least 50 weight percent of the ethyl acrylate product residue separated from the substantially pure ethyl acrylate product through the same wiped-film evaporator unit used for the sulfuric acid residue.

SUMMARY OF THE INVENTION

The process of the present invention involves passing at least 50 weight percent of the ethyl acrylate product residue from the finishing distillation tower together with a minor portion of the sulfuric acid residue obtained from the recovery distillation tower through a wiped-film evaporator. The wiped-film evaporator is operated to heat the material entering to a temperature in the range from about 300° F. to about 360° F. and to cool the material in the last or withdrawal section(s) of the evaporator to a temperature in the range from about 230° F. to about 280° F.

Ethyl acrylate product and acrylic acid reactant can be recovered from the treatment of the sulfuric acid residue and the ethyl acrylate product residue in the wiped-film evaporator. At the same time the treatment of the sulfuric acid residue and ethyl acrylate product residue provides processing improvements in the prevention of the foaming of the sulfuric acid residue. Additionally, polymerization initiators and other impurities are removed from the reaction system to ensure a smooth and extended continuous operation. This in combination with the other described improvements provide significantly improved overall yields and efficiencies of the process of this invention.

DETAILED DESCRIPTION OF THE INVENTION

Figure 1:
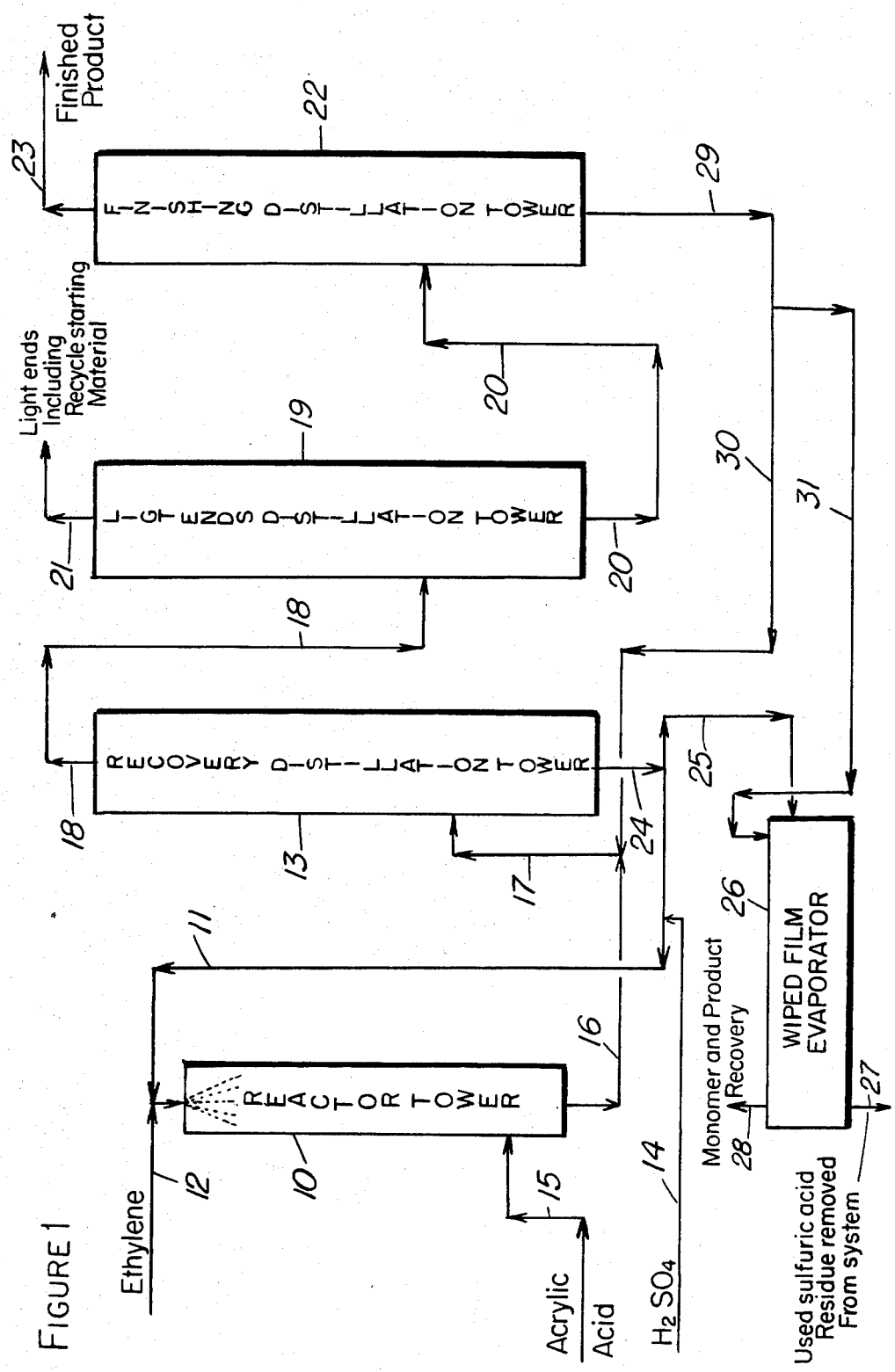
FIG. 1 is a simplified schematic flow sheet exemplifying the preparation of ethyl acrylate from ethylene and anhydrous acrylic acid in the presence of substantially anhydrous sulfuric acid showing the use of a wiped-film evaporator for removal of a portion of the spent sulfuric acid residue and at least about 50 weight percent of the ethyl acrylate product residue from the finishing distillation tower.

The process of the present invention is schematically represented in FIG. 1, in which a combination of substantially anhydrous sulfuric acid medium supplied through line 11 and ethylene supplied through line 12 is sprayed into reactor tower 10 and mixed. The sulfuric acid medium is comprised of sulfuric acid residue or bottoms from the product recovery distillation tower 13 along with make-up sulfuric acid added through line 14. The sulfuric acid residue (sometimes referred to in the industry as "black acid") recovered from the recovery distillation tower 13 is a mixture of various compounds and contains sulfuric acid, intermediate sulfates from the reaction of ethylene and sulfuric acid, unreacted acrylic acid, some small amounts of ethyl acrylate and various other compounds.

In the reactor tower 10, the main reaction of concern is the liquid phase reaction of ethylene-enriched liquid with sulfuric acid to give various intermediate sulfate salts, such as ethyl hydrogen sulfate and diethyl sulfate, which will then further react with acrylic acid, supplied through line 15 to form ethyl acrylate. Adequate mixing of the reaction mixture in the reaction tower 10 can be obtained by mechanical stirring or recycle of the reaction products. (Neither mixing techniques are shown in the drawing). The reactants' residence time in the reactor tower 10 must be sufficient to obtain substantially (preferably at least a 90% completion) complete reaction of ethylene and acrylic acid. Temperatures in the reaction tower should be maintained within the range of about 100° C. to about 150° C., preferably 110° C. to 130° C. and the pressure should be maintained within the range of about 100 to about 300 psig, preferably 130 to 200 psig.

The reaction products from the reactor tower 10 are withdrawn through line 16 and passed through a pressure reduction valve (not shown) and thence to the recovery distillation tower 13. The distillation section of the recovery distillation tower may be of conventional design, and may contain packing, sieve type trays or dual flow trays. The distillation section should contain an equivalent of at least four theoretical trays. A vacuum is maintained in the recovery distillation tower 13 by conventional means so that the pressure is less than about 200 mm of mercury absolute, and preferably within the range of 20 to 150 mm of mercury absolute. The still pot temperature should be maintained within the range of about 100° C. to about 170° C., preferably 110° C. to 130° C., and the still head temperature within the range of about 28° C. to about 45° C., preferably 30° C. to 40° C.

The feed line 17 to the recovery distillation tower 13 is directed preferably to the lower third, and more preferably to the base of the tower. In the recovery distillation tower 13, the light ends of crude ethyl acrylate, comprising mainly of ethyl acrylate, small amounts of unreacted ethylene and other uncondensables, are removed overhead through line 18 and passed to the light ends distillation tower 19 (of conventional distillation design). Partially purified ethyl acrylate product is removed as bottoms through line 20. A stream comprising mainly unreacted ethylene is removed from the light ends distillation tower 19 through line 21 and may be disposed of or recycled (not shown) to the reactor tower 10 as desired, although if recycled a scrubbing to remove sulfur oxides is recommended. As pointed out above, operation according to the present invention generally results in a very small amount of unreacted ethylene such that the amounts of ethylene removed through line 21 will be relatively small. The partially purified ethyl acrylate product recovered through line 20 is further treated by fractionation in the finishing distillation tower 22 to obtain, through line 23, a substantially pure ethyl acrylate having a purity greater than 95 percent, preferably about 99.9 percent or higher.

In operating the recovery distillation tower 13, the residence time of the reaction products in the base of the tower should be as low as possible because at temperatures required in the reboiler for vaporization some polymerization may occur. It is desirable to have a feed stream lean in acrylic acid being fed to the recovery distillation tower since this will result in less polymer formation.

The sulfuric acid residue or black acid stream referred to above, containing sulfuric acid, intermediate sulfates, unreacted acrylic acid and the like is removed as bottoms residue from the recovery distillation tower 13 through line 24. A blowdown of a minor portion of the bottoms stream or sulfuric acid residue which is approximately 1 to 5 percent by weight of the total sulfuric acid residue is taken by means of line 25 so as to prevent the buildup of impurities in the system. The remaining major portion of the sulfuric acid residue can be recycled through line 11 to the reactor tower 10 in combination with ethylene.

This minor portion of the sulfuric acid residue is passed through line 25 to a horizontal wiped-film evaporator 26 which heats the sulfuric acid residue to temperatures in the range from about 300° F. to about 360° F., and preferably 325° F. to 350° F. in the initial portion of the wiped-film evaporator 26. At the last or withdrawal section(s) of the wiped-film evaporator 26, the spent sulfuric acid residue is cooled to temperatures in the range from about 230° F. to about 280° F., and preferably 240° F. to 270° F., for removal from the system through line 27. During the treatment of the sulfuric acid residue for the process of this invention, the wiped-film evaporator 26 is maintained under reduced pressure in the range from about 40 to about 150 mm of mercury absolute and preferably in the range from about 50 to 80 mm of mercury absolute. Ethyl acrylate and acrylic acid can be recovered through line 28 from the wiped-film evaporator 26. The preferred procedure for the ethyl acrylate and acrylic acid removed from the wiped-film evaporator is to recycle these products to the recovery distillation tower 13 for reprocessing.

Although not shown on the drawing, the addition of a polymerization inhibitor is generally desirable when producing or purifying ethyl acrylate. Such inhibitors are known, and can be materials absolute in the reaction medium or soluble in the product obtained from the recovery distillation tower. Suitable polymerization inhibitors include hydroquinone, phenothiazine, the methyl ether of hydroquinone, quinone and the like. The polymerization inhibitor can be introduced to the reaction vessel in the used sulfuric acid residue or through any other convenient part of the system. It is required that the inhibitor be added to lines 18, 21 and 23. The inhibitor can be added in line 18 from which it is carried out through to the light ends distillation tower 19, then into the finishing distillation tower 22 and into the residue of the finishing distillation tower 22.

The ethyl acrylate product residue of the finishing distillation tower 22 containing the polymerization inhibitor is removed through line 29 and the ethyl acrylate product residue can be divided wherein at least 50 weight percent of the residue can be passed through line 31 into the wiped-film evaporator 26 for recovery of organic products such as ethyl acrylate and acrylic acid. The preferred process is to pass all of the ethyl acrylate product residue into the wiped-film evaporator 26. If only a portion of the ethyl acrylate product residue is passed into the wiped-film evaporator 26, the remaining portion can be passed through line 30 into line 17 which is combined with the reaction products passed into the recovery distillation tower 13 and finally combined with the sulfuric acid residue to be recycled through line 24 back to the reactor tower 10. If all of the ethyl acrylate product residue from the finishing distillation tower is recycled to the recovery distillation tower 13, the result can be a greater degree of fouling in the recovery distillation tower caused by black acid viscosity increase and a subsequent loss of product polymer. Passing the ethyl acrylate product residue of the finishing distillation tower to the wiped-film evaporator, an improvement in the overall process efficiency is achieved since the fouling of the recovery distillation tower is decreased with less polymer being formed.

The wiped-film evaporator which can be used in the process of the present invention can be a vertical or horizontal unit. For this invention, a horizontal unit is preferred. Typical of the units that can be used and are known are the types described in a three part report in *Chemical Engineering*, Sept. 13, 1965, pages 175–190, entitled "Agitated Thin-Film Evaporators". The one essential criterion of the wiped-film evaporator used in this process is the capability of cooling the latter section of the evaporator to provide a residue having specific temperature ranges as described herein. Normally, the use of a wiped-film evaporator is for separating and recovering the low boiling materials from the high boiling viscous materials using as much heat as possible over as much heating surface as possible to achieve and maintain high temperatures for fast and efficient separation. Under these conditions one would normally not consider cooling any portion of the treating surface of the wiped-film evaporator. The unique problem of this invention in the treatment of the combination of the viscous sulfuric acid residue and the ethyl acrylate product residue, is the foaming of the residue in the latter section(s) of the wiped-film evaporator on heating at temperatures in the range from about 300° F. to about 360° F. These temperatures are needed to effectively and efficiently separate ethyl acrylate and acrylic acid from the sulfuric acid residue. The foaming of the treated residue can be so severe that the foamed material can back up into the purification system requiring the shut down of the process. This foaming can be substantially eliminated by cooling the last or withdrawal section(s) of the wiped-film evaporator to temperatures in the range from about 230° F. to about 280° F. It is indeed a surprising result wherein a wiped-film evaporator is used efficiently by heating the initial sections of the unit and cooling the last or withdrawal sections of the unit.

Figure 2:
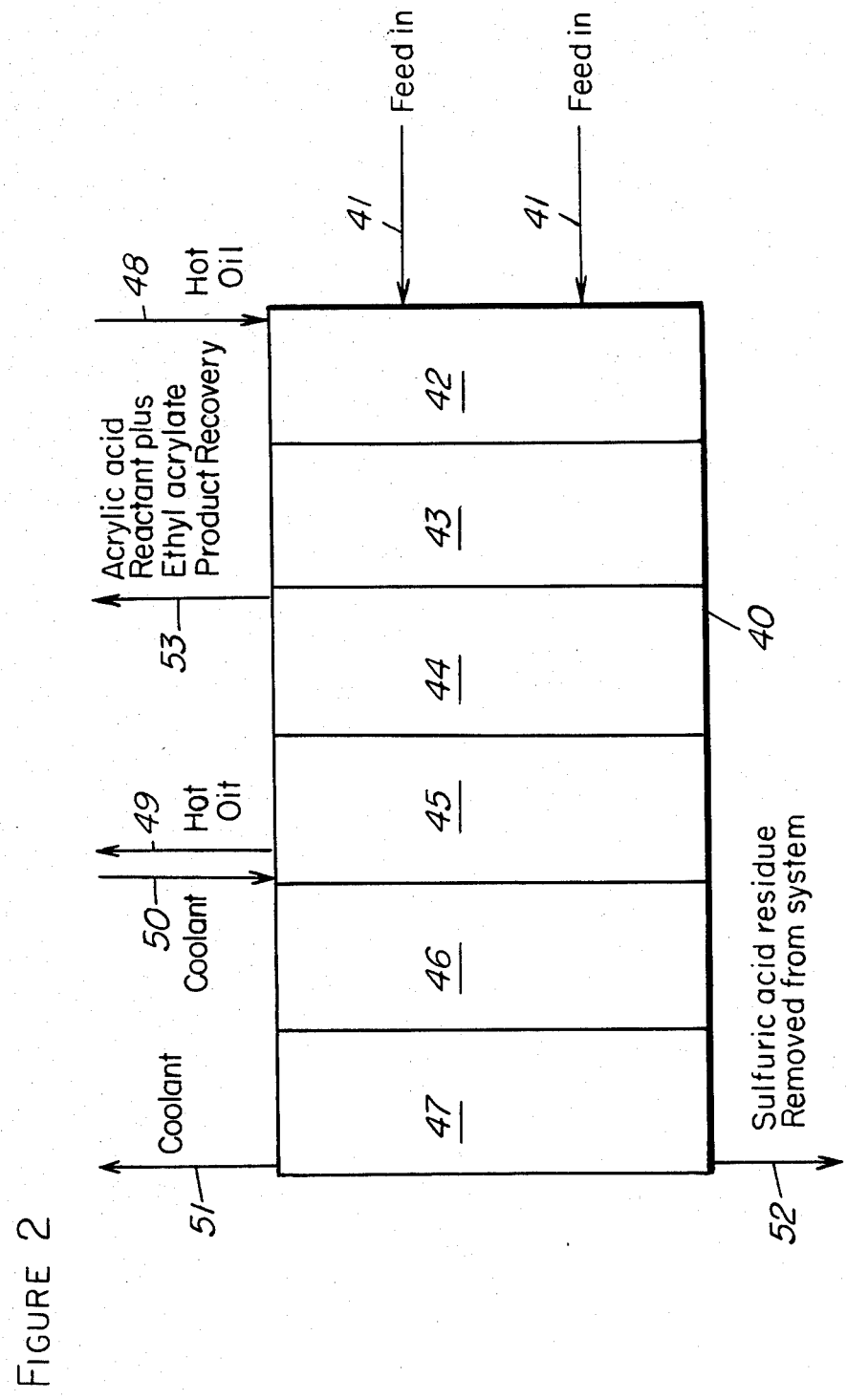
FIG. 2 is a schematic representation of a wiped-film evaporator which heats the feed of sulfuric acid residue and ethyl acrylate product residue in the initial sections of the evaporator and cools the spent sulfuric acid residue and ethyl acrylate product residue at the last or withdrawal sections.

FIG. 2 is a schematic representation of the wiped-film evaporator 40 which can be used in the present invention. The sulfuric acid residue and ethyl acrylate product residue are fed through lines 41 to the evaporator 40 which contains various sections 42 through 47. Sections 42 through 45 can be heated by hot condensate steam entering the jacket of section 42 through 48 to heat the sulfuric acid residue to temperatures in the range from about 300° F. to about 360° F., and preferably in the range from about 325° F. to about 350° F. The condensate steam can be removed from the jacket section 45 through line 49 for reuse. Sections 46 and 47 can be cooled by a coolant such as steam, water and the like entering through line 50 to cool the sulfuric acid residue to temperatures in the range from about 230° F. to about 280° F., preferably in the range from about 240° F. to about 270° F. Care must be exercised that the coolant is not excessively cool to prevent thermal stressing resulting in metal fatigue and/or mechanical damage to the unit. The coolant can be removed through line 51 for reuse. The spent sulfuric acid residue and ethyl acrylate product residue can be removed from evaporator 40 and the system through line 52. The acrylic acid reactant and ethyl acrylate product can be removed from line 53.

To illustrate the process of this invention, referring to the description of FIG. 1 and using the conditions as described, 3055 pounds per hour of ethylene and 7850 pounds per hour of acrylic acid are added to the reactor tower 10 into which 92,967 pounds per hour of sulfuric acid medium is recycled with 879 pounds per hour of anhydrous sulfuric acid makeup is added. From the recovery distillation tower 13, 14,199 pounds per hour of crude ethyl acrylate product are obtained overhead through line 18. From the bottom of the recovery distillation tower 13, 2789 pounds per hour of sulfuric acid residue are removed from the recycle sulfuric acid medium and passed through the wiped-film evaporator 26. 14,199 pounds per hour of crude ethyl acrylate product is passed through line 18 to the light ends distillation tower 19. 157 pounds per hour of light ends are recovered in the overhead line 21 and 13,962 pounds per hour of partially purified ethyl acrylate product is passed through line 20 to the finishing distillation tower 22. 9380 pounds per hour of purified ethyl acrylate are recovered through line 23 and 4582 pounds per hour of ethyl acrylate product residue are recovered through line 29 and passed through line 31 to the wiped-film evaporator 26.

2789 pounds per hour of sulfuric acid residue and 4582 pounds per hour of ethyl acrylate product residue are passed through the wiped-film evaporator 26. 5188 pounds per hour of ethyl acrylate and 215 pounds per hour of acrylic acid are recovered through 28 from the wiped-film evaporator. The material removed from the wiped-film evaporator and the reaction system are 879 pounds per hour of sulfuric acid and 1099 pounds per hour of polymeric acrylates among other products.

The wiped-film evaporator was operated under reduced pressure of 70 mm absolute. The temperatures of the oil used in the initial sections of the wiped-film evaporator were maintained in the range from 360° F. to 370° F. The coolant in the last or withdrawal section(s) of the wiped-film evaporator was hot condensate (steam) maintained at temperatures in the range from 250° F. to 270° F.

What is claimed is:
1. In a process for the production of ethyl acrylate comprising the steps of:
   (a) reacting ethylene and acrylic acid in the presence of sulfuric acid to form a reaction product;
   (b) separating said reaction product into crude ethyl acrylate and a sulfuric acid residue;

(c) recycling a major portion of said sulfuric acid residue of step (b) to step (a) and passing the remaining portion of said residue from step (b) through a wiped-film evaporator which is heated in its initial sections so that said sulfuric acid residue reaches a temperature in the range from about 300° F. to about 360° F., and cooled in its withdrawal section(s) to cool said sulfuric residue to a temperature in the range from about 230° F. to about 280° F., thereby removing spent sulfuric acid residue from the system;

(d) separating the light end materials from said crude ethyl acrylate and other reaction products to obtain a partially purified ethyl acrylate; and (e) separating and recovering a substantially pure ethyl acrylate from said partially purified ethyl acrylate leaving an ethyl acrylate product residue;

the improvement comprising passing at least about 50 weight percent of said ethyl acrylate product residue of step (e) to said wiped-film evaporator of (c) and passing the remaining portion of said ethyl acrylate product residue to the separation step (b).

2. The process of claim 1 wherein all of the ethyl acrylate product residue of step (e) is passed to the wiped-film evaporator of (c).

3. The process of claim 1 wherein the temperature of said sulfuric acid residue and said ethyl acrylate product residue in the initial section of said wiped-film evaporator is in the range from about 325° F. to about 350° F. and the temperature of said sulfuric acid residue and said ethyl acrylate product residue in the withdrawal section(s) of said wiped-film evaporator is in the range from about 240° F. to about 270° F.

* * * * *